United States Patent
Matsumoto et al.

(10) Patent No.: US 6,878,239 B1
(45) Date of Patent: Apr. 12, 2005

(54) PROCESS FOR INHIBITING A POLYMERIZATION IN A VACUUM SECTION OF AN EASILY POLYMERIZABLE COMPOUND PURIFICATION SYSTEM

(75) Inventors: Yukihiro Matsumoto, Kobe (JP); Takeshi Nishimura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 251 days.

(21) Appl. No.: 09/587,387

(22) Filed: Jun. 5, 2000

(30) Foreign Application Priority Data

Jun. 3, 1999 (JP) .......................................... 11-156656

(51) Int. Cl.[7] .............................. B01D 3/10; B01D 3/34; C07C 69/54; C07C 57/025
(52) U.S. Cl. ............................ 203/8; 203/91; 203/100; 203/DIG. 14; 203/DIG. 21; 560/218; 562/600
(58) Field of Search ........................ 203/8, 91, DIG. 14, 203/100, DIG. 21, 6, 9; 560/218, 205; 562/600

(56) References Cited

U.S. PATENT DOCUMENTS

| | | | | |
|---|---|---|---|---|
| 3,674,651 A | * | 7/1972 | Otsuki et al. ................ | 203/8 |
| 3,951,756 A | * | 4/1976 | Dirks et al. .................. | 203/95 |
| 4,113,574 A | * | 9/1978 | Schumacher et al. ......... | 203/8 |
| 4,182,658 A | * | 1/1980 | Watson ......................... | 203/9 |
| 4,210,493 A | * | 7/1980 | Stewart et al. ................ | 203/8 |
| 4,301,298 A | | 11/1981 | Horlenko et al. | |
| 4,369,097 A | | 1/1983 | Nezu et al. | |
| 5,159,106 A | | 10/1992 | Ritter et al. | |
| 5,207,874 A | * | 5/1993 | Hess et al. .................... | 203/8 |
| 5,770,021 A | * | 6/1998 | Hego et al. ................... | 203/8 |
| 5,855,743 A | * | 1/1999 | Herbst et al. ................ | 203/74 |
| 6,398,918 B1 | * | 6/2002 | Popov ........................... | 203/2 |
| 6,436,245 B1 | * | 8/2002 | Nishimura et al. ........... | 203/99 |
| 6,525,216 B1 | * | 2/2003 | Nishimura et al. ........... | 562/542 |
| 6,596,129 B1 | * | 7/2003 | Yoneda et al. ................ | 203/2 |

FOREIGN PATENT DOCUMENTS

| JP | 10-204030 | 8/1998 |
|---|---|---|
| WO | 98/35736 | 8/1998 |

OTHER PUBLICATIONS

Database WPI, Section Ch, Week 8311, Derwent Publications Ltd., London, Great Britain, An 1983–26134k, XP002239392, Abstract of JP 58 019393 A, Feb. 4, 1983.

* cited by examiner

Primary Examiner—Virginia Manoharan
(74) Attorney, Agent, or Firm—Wenderoth, Lind & Ponack, L.L.P.

(57) ABSTRACT

A process for inhibiting a polymerization of an easily polymerizable compound purification system is disclosed.

According to the present invention, the polymerization of the easily polymerizable compound such as (meth)acrylic acid and (meth)acrylate flowed into a vacuum section can be inhibited by contacting a liquid containing a polymerization inhibitor with the compound directly in the vacuum section.

When the vacuum section includes a gas and liquid contact chamber (usually a condenser), the liquid containing a polymerization inhibitor may be supplied to the chamber. When the vacuum section includes a liquid ejector and/or a nash pump as a vacuuming device, the liquid containing a polymerization inhibitor may be circulated by the liquid ejector and/or the nash pump for reducing a pressure of a purifying section. Examples of easily polymerizable compounds are (meth)acrylic acid and (meth)acrylates. The process of the invention is capable of inhibiting the polymerization of the easily polymerizable compound such as (meth)acrylic acid and (meth)acrylate in a vacuum section of a purifying system. The system of the invention is suitable for purifying the easily polymerizable compound.

9 Claims, 4 Drawing Sheets

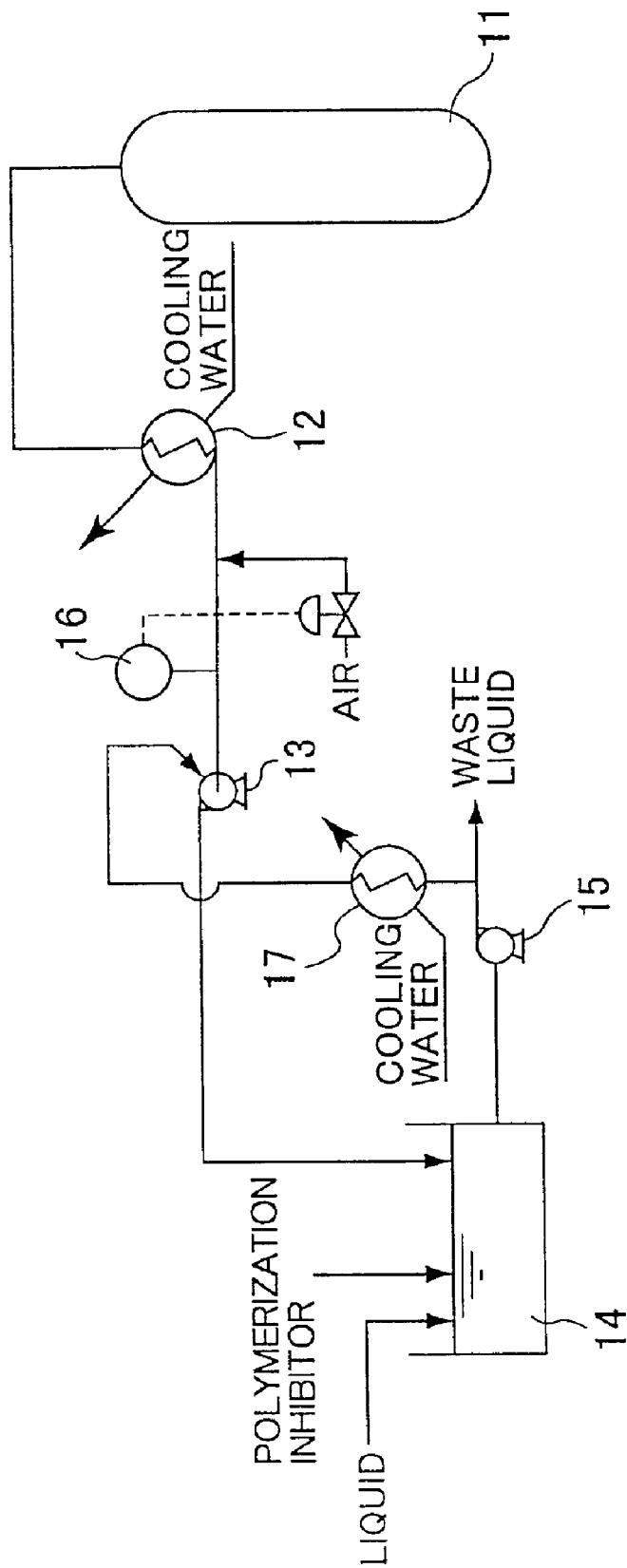

PROCESS FOR INHIBITING A POLYMERIZATION IN A VACUUM SECTION OF AN EASILY POLYMERIZABLE COMPOUND PURIFICATION SYSTEM

BACKGROUND OF THE INVENTION

1. Field of the Invention

The present invention relates to a process for inhibiting a polymerization in a vacuum system, which is used for purifying an easily polymerizable compound such as (meth) acrylic acid and (meth)acrylate under a reduced pressure. The invention also relates to the easily polymerizable compound purification system.

2. Description of the Related Art

In distillation operations of the easily polymerizable compound such as (meth)acrylic acid and (meth)acrylate, polymerization of the easily polymerizable compound must be avoided during distillation. To this end, the pressure inside a distillation column is reduced and the inside temperature is decreased as much as possible, and a polymerization inhibitor such as hydroquinone and phenothiazine, or a gas containing molecular oxygen is used for inhibiting a polymerization.

FIG. 1 is a schematic illustration of a conventional process for the purification of the easily polymerizable compound. This process includes a purifying section which comprises a distillation column 1 and a condenser 2 and a vacuum section which comprises a steam ejector E1, E2 and E3 for reducing a pressure of a purifying section, a barometric condenser 3, surface condensers 4 and 5 and a ejector seal tank 6.

An easily polymerizable compound is usually distilled in the distillation column 1 under a reduced pressure. The pressure inside the distillation column 1 is controlled by the closing and opening of an air regulating valve 8, while the air regulating valve 8 is controlled on the basis of measurements obtained by a pressure gauge 7. Most of the resulting distilled components is condensed through a condenser 2. The exhaust gas from the condenser 2 flows into a vacuum section by the aid of a steam ejector E1 which is reducing the pressure of a purifying section. The gas usually contains the easily polymerizable compound which is not condensed through the condenser 2 and other noncondensing gases. The gas and steam through the steam ejector E1 are condensed in a barometric condenser 3 by contacting the gas with a cooling liquid directly. The resulting condensate is withdrawn into an ejector seal tank 6 and a remaining gas is sucked into the second steam ejector E2. The gas and steam from the second steam ejector E2 are condensed through a surface condenser 4 and the resulting condensate is withdrawn into the ejector seal tank 6 and the remaining gas is sucked into the third steam ejector E3. In the case of a surface condenser, the gas is condensed without direct contact with a cooling water. The gas from a third ejector E3 is condensed through a surface condenser 5 attached at the downstream side of third ejector E3. Generally, both the resulting condensate and a remaining gas are liquid-sealed by the ejector seal tank 6. In some processes, the gas is not liquid-sealed at a final stage.

FIG. 2 is an illustration of another conventional process for the purification of the easily polymerizable compound. This process includes a purifying section which comprises a distillation column 11 and a condenser 12 and a vacuum section comprising a nash pump 13 as a vacuuming device, a pump 15 and a tank 14 and a cooler 17. The easily polymerizable compound is distilled in a distribution column 11 and the resulting distilled compound is condensed through a condenser 12. The exhaust gas from the condenser 12 flows into a vacuum section by the aid of the nash pump 13 reducing a pressure of a purifying section. The gas usually contains the easily polymerizable compound which is not condensed through the condenser 12 and a noncondensing gas. The gas is usually sealed by the liquid which is circulated from a tank 14 by the nash pump 13 and the pump 15.

According to the conventional process, the gas exhausted from a condenser connected to a distillation column contains an easily polymerizable compound such as (meth)acrylic acid and (meth)acrylate. The easily polymerizable compound is liable to polymerize, and the resulting polymer clogs a condenser, a liquid ejector, or a nash pump, and the vacuum section is frequently forced to stop.

SUMMARY OF THE INVENTION

An object of the invention is to provide a process which is capable of inhibiting the polymerization in a vacuum section of an easily polymerizable compound purification system.

Another object of the invention is to provide an system which is free from the problems residing in the prior art.

According to an aspect of the invention, a process for inhibiting polymerization in a vacuum section of an easily polymerizable compound purification system comprises the step of permitting a gas containing an easily polymerizable compound to flow into a gas and liquid contact chamber from a purifying section, the gas and liquid contact chamber being supplied with a liquid containing a polymerization inhibitor.

According to another aspect of the invention, a system for purifying an easily polymerizable compound comprises:

a column for purifying an easily polymerizable compound;

a vacuum portion for vacuuming a gas containing the easily polymerizable compound from the column; and a liquid supply equipment for supplying a liquid containing a polymerization inhibitor to the vacuum portion to thereby come into contact with the gas.

BRIEF DESCRIPTION OF THE DRAWINGS

FIG. 4 is a schematic illustration of another system for purification of an easily polymerizable compound according to another embodiment of the invention.

DESCRIPTION OF THE PREFERRED EMBODIMENT

The subject-matter of the present invention is that the polymerization in a vacuum section of an easily polymerizable compound purification system can be inhibited by contacting a liquid containing a polymerization inhibitor with a gas containing an easily polymerizable compound in a gas and liquid contact chamber. The liquid is contacted with the compound directly before the compound begins to polymerize in the vacuum section. The invention has been accomplished based on these findings.

Figure 3:
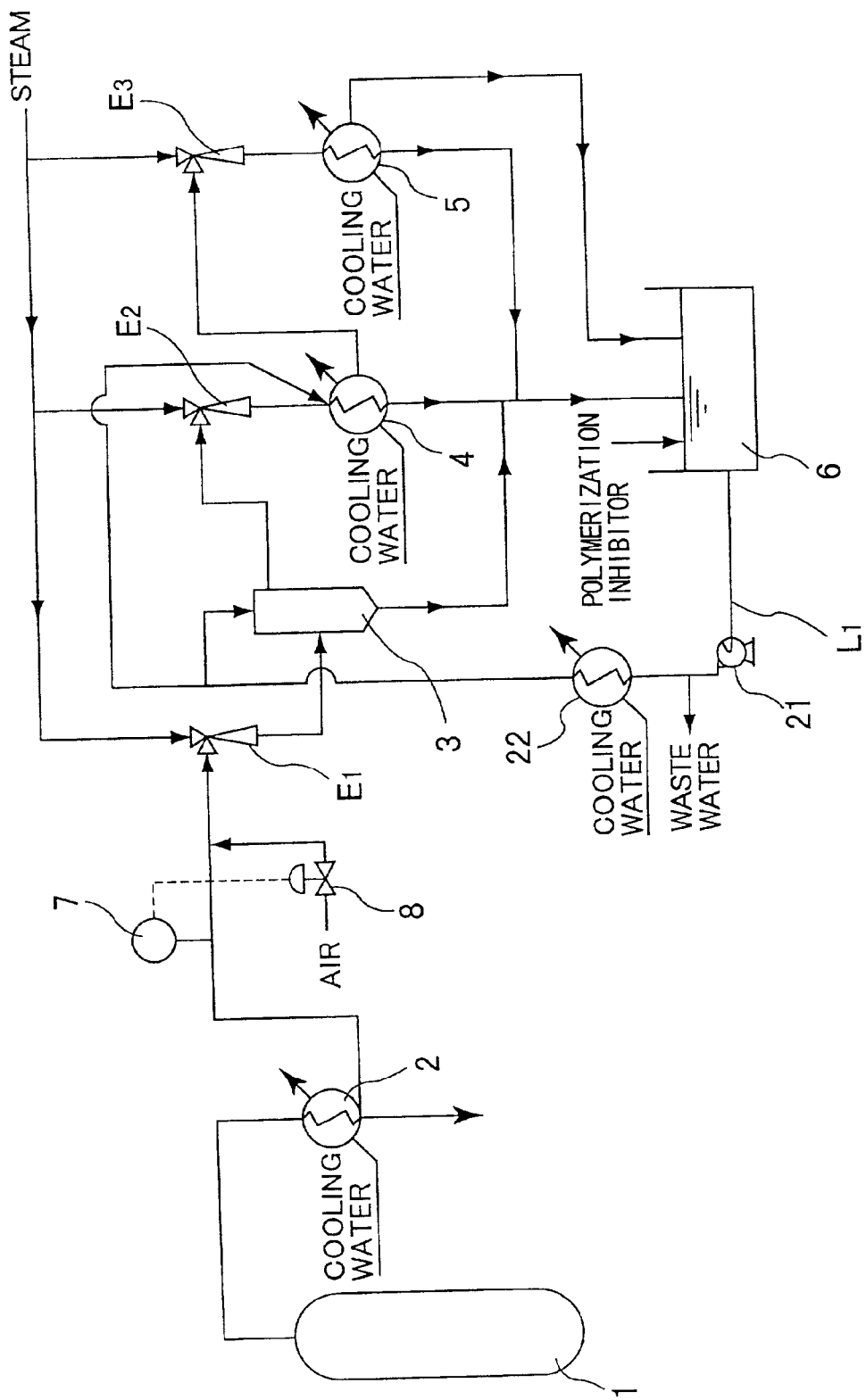
FIG. 3 is a schematic illustration of a system for purification of an easily polymerizable compound according to another embodiment of the invention.

FIG. 3 is a schematic diagram illustrating the invented process and system for the inhibiting the polymerization in the vacuum section of the easily polymerizable compound purification system.

The system shown in FIG. 3 includes a purifying section which comprises a distillation column 1, a condenser 2, a pressure gauge 7, an air regulating valve 8 and pipes connecting them and a vacuum section which comprises a steam ejector E1, E2 and E3 as a vacuuming device, gas and liquid contact chambers 3, 4 and 5, a cooler 22, a pump 21, an ejector seal tank 6 and pipes connecting them. In the system, the pipes must be connected so that a condensed liquid of the gas containing the easily polymerizable compound does not accumulate. For example, a vacuuming nozzle and a exhausting nozzle of the gas and liquid chamber are preferably set horizontally or downward below horizontal. The vacuum section comprises a vacuum portion and a liquid supply equipment.

In this embodiment, the steam ejector and the gas and liquid contact chamber constitutes the vacuum portion and the pump and the ejector seal tank constitutes the liquid supply equipment.

According to this process of the invention, a polymerization inhibitor is added to a liquid in the ejector seal tank 6, and the liquid containing a polymerization inhibitor is supplied from the ejector seal tank 6 through a line L1 to the inside of the gas and liquid contact chambers 3 and 4 by the aid of a pump 21 to inhibit the polymerization of the easily polymerizable compound in the vacuum section. Examples of the polymerization inhibitors for the process of the invention are hydroquinone, methoquinone, manganese acetate, phenothiazine, nitrosophenol, cupferron, dibutyl dithio carbamic acid copper salt and N-oxyl compounds.

According to the process of the invention, the easily polymerizable compound is distilled in the distillation column 1 under the reduced pressure. Examples of easily polymerizable compounds are (meth)acrylic acids and (meth)acrylates. Examples of (meth)acrylates are methyl (meth)acrylate, ethyl(meth)acrylate, isopropyl(methy) acrylate, n-propyl(meth)acrylate, isobutyl(meth)acrylate, 2-hydroxyethyl(meth)acrylate, hydroxypropyl(methy) acrylate, dialkylaminoethyl(meth)acrylate.

Most of the distilled compound is condensed through a condenser 2. The exhaust gas from the condenser 2 flows into a vacuum section by the aid of a steam ejector E1 which is reducing a pressure of a purifying section. The gas usually contains the easily polymerizable compound which is not condensed through the condenser 2 and other noncondensing gases. The gas flows into the gas and liquid contact chamber 3 through the steam ejector E1 and is contacted with the liquid containing a polymerization inhibitor which is supplied from the ejector seal tank 6. The gas and liquid contact chamber may be set between the purifying section and the vacuum section. Preferably the gas and liquid contact chamber is a condenser such as a barometric condenser and a surface condenser in a vacuum section.

When the gas and liquid contact chamber is a barometric condenser, the liquid is supplied to cool the barometric condenser and contacted with the compound directly in the condenser so as to inhibit the polymerization of the compound.

When the gas and liquid contact chamber is a surface condenser, the inside surface of the surface condenser is wetted uniformly with the liquid. The liquid is preferably sprayed onto the overall surface of the surface condenser. Such surface condensers include horizontal condensers and vertical condensers, where condensation is performed inside a tube (inside condensation type) or outside the tube (outside condensation type). From the viewpoint of uniform wetting, a vertical condenser is preferred to a horizontal condenser, and an inside condensation type is preferred to an outside condensation type.

When the two or more gas and liquid contact chambers are included in the vacuum section, preferably the liquid containing the polymerization inhibitor should be supplied to the first gas and liquid contact chamber or to both of the first and the second gas and liquid chambers, because the first gas and liquid chambers usually contains a gas including large amount of the easily polymerizable compounds. In this case, barometric condensers are preferred to surface condensers for the gas and liquid contact chamber.

The vacuum section can include a liquid ejector and/or a nash pump instead of the steam ejector for reducing a pressure of the purifying section. The Liquid ejectors and nash pumps are applied for reducing a pressure of the purifying section in the range of an absolute pressure from 6.7 kPa (50 mmHg) to 101 Kpa (760 mmHg). On the other hand, the steam ejector can be employed for almost overall ranges of the pressure of the purifying section by adjusting several stages of ejectors (usually, one to five ejectors).

FIG. 4 is a schematic illustration of another embodiment of the invented process for the distillation of the easily polymerizable compound using a nash pump. This process includes a purifying section which comprises a distillation column 11, a condenser 12, a pressure gauge 16, and a vacuum section which comprises a nash pump 13, a pump 5, a tank 14 and a cooler 17. The vacuum section comprises a vacuum portion and a liquid supply equipment. In this embodiment, the nash pump 13 constitutes the vacuum portion and the pump 15, the tank 14 and the cooler 17 constitutes the liquid supply equipment. The vacuum portion can employ a combination of the nash pumps, the steam ejectors and the liquid ejectors.

According to this process of the invention, a polymerization inhibitor is added to a liquid in the tank 14, and the liquid is circulated by the nash pump 13 and the pump 15 for reducing a pressure of the purifying section. The gas containing the easily polymerizable compound such as (meth) acrylic acid and (meth)acrylate is sucked into the nash pump 13 and sealed by the liquid circulated from the tank 14 by the aid of the pump 15 so as to inhibit the polymerization of the compound.

When a portion of the liquid is exhausted as a waste gas by the flow rate of the gas, an additional liquid containing the polymerization inhibitor is supplied to compensate for the amount of the waste liquid. Preferably the additional liquid is supplied to avoid increasing the concentration of the compound in the liquid. The waste liquid containing the compound is preferably recycled for recovering the compound and inhibiting a polymerization of a purification section such as an absorbing column, a distillation column and a stripping column.

The invention as thus configured provides a process for inhibiting the polymerization in a vacuum section for purifying an easily polymerizable compound such as (meth) acrylic acid and (meth)acrylates and an system for purifying an easily polymerizable compound.

The present invention will now be illustrated in more detail with reference to a comparative example and an inventive example below, which are not intended to limit the scope of the invention.

EXAMPLE

A purifying system shown in FIG. 3 includes a purifying section which comprises a distillation column 1, a condenser 2, a pressure gauge 7, an air regulating valve 8 and a vacuum section which comprises a steam ejector E1, E2 and E3 as a vacuuming device, a barometric condenser 3, surface condensers 4 and 5 as a gas and liquid contact chamber, a cooler 22 and a pump 21 and an ejector seal tank 6. Using the system, a liquid containing acrylic acid was put into the distillation column 1, and distillation was continuously performed by operating the system at an overhead absolute pressure of 3.3 kPa (25 mm Hg), and distilling off acrylic acid as an overhead product by supplying a liquid containing 100 ppm of hydroquinone as a polymerization inhibitor to the barometric condenser 3 and the surface condenser 4 shown in FIG. 3. As a result, the operation could be contained for one month without a problem. The system was stopped to be inspected, and small amounts of the polymer were observed to attach to the first barometric condenser and the second surface condenser.

COMPARATIVE EXAMPLE

Figure 1:
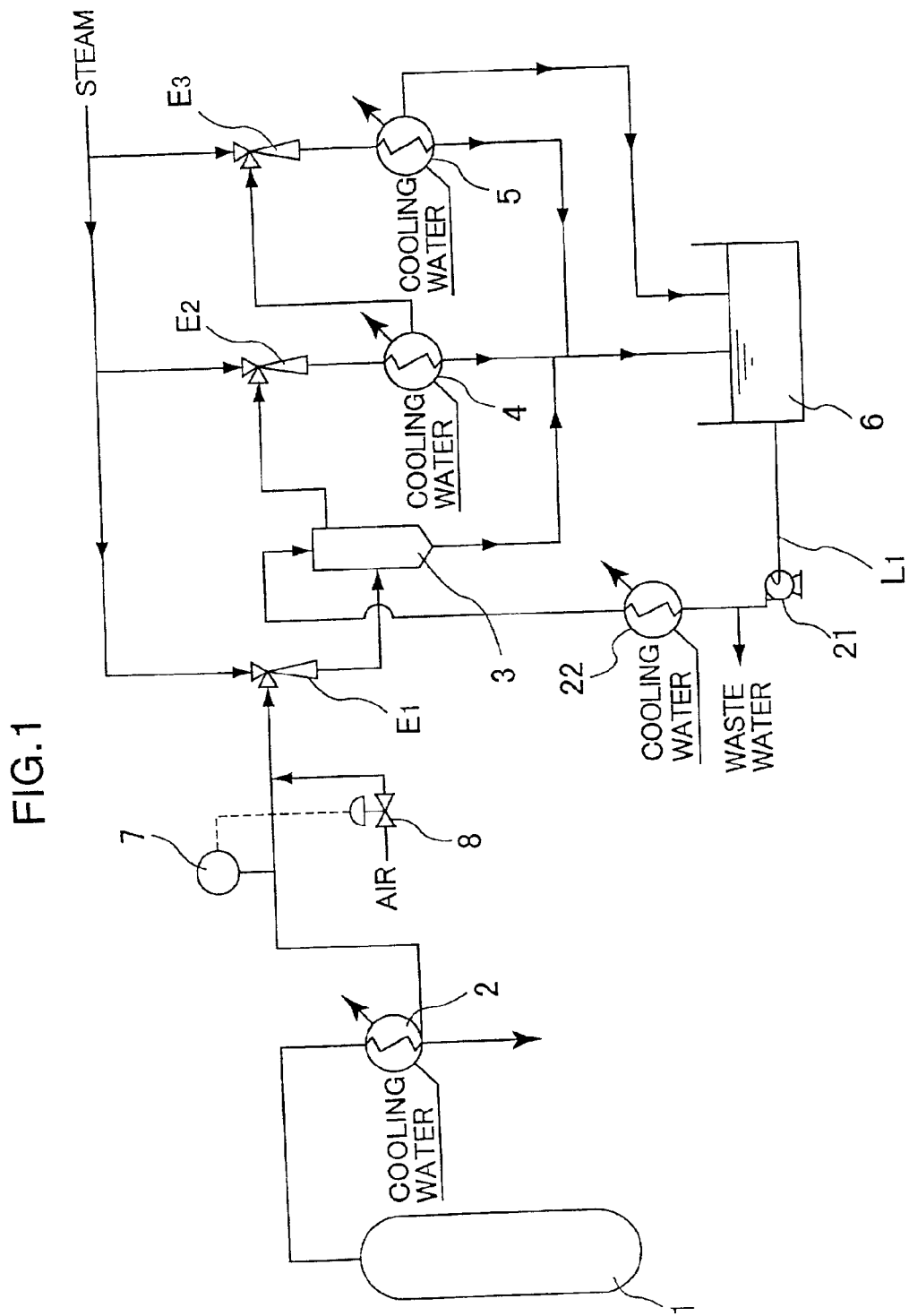
FIG. 1 is a schematic illustration of a conventional system for purification of an easily polymerizable compound.
Figure 2:
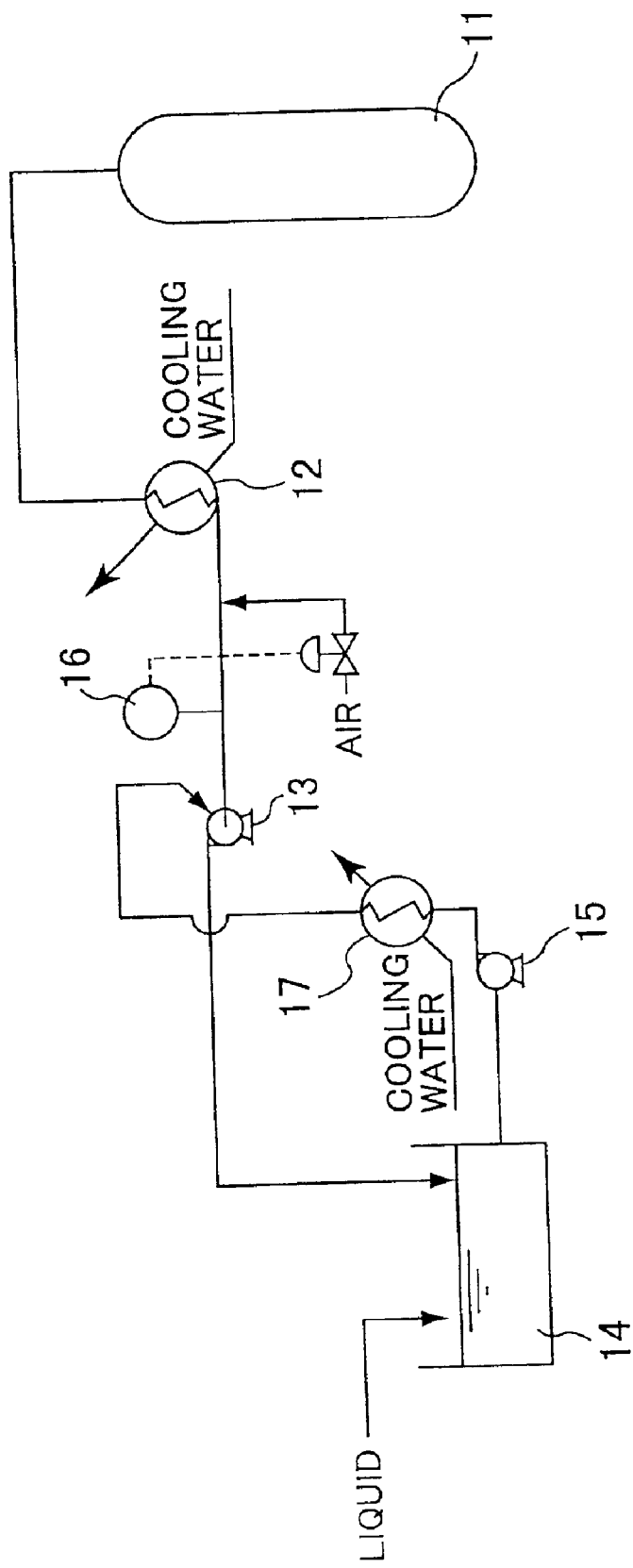
FIG. 2 is a schematic illustration of another conventional system for purification of an easily polymerizable compound.

A purifying system shown in FIG. 1 includes a purifying section which comprises a distillation column 1 and a condenser 2 and a vacuum section which comprises a steam ejector E1, E2 and E3 for reducing a pressure of a purifying section, a barometric condenser 3, surface condensers 4 and 5 and a ejector seal tank 6. Using this system, a liquid containing acrylic acid was put into the distillation column 1, and distillation was continuously performed by operating the system at an overhead absolute pressure of 3.3 kPa (25 mm Hg), and distilling off acrylic acid as an overhead product without using a polymerization inhibitor. Eight days into the operation, the overhead pressure could not be retained at a constant level of 3.3 pKa (25 mm Hg), and the pressure started to increase then. The vacuum section was forced to stop because of the polymerization of acrylic acid.

This application is based on patent application No. 11-156656 filed in Japan, the contents of which is hereby incorporated by reference.

Other embodiments and variations will be obvious to those skilled in the art, and this invention is not to be limited to the specific matters stated above.

What is claimed is:

1. A process for inhibiting polymerization in a vacuum section of an easily polymerizable compound purification system, wherein the purification system comprises:
    a purifying section, including a distillation column and a condenser, and
    the vacuum section, including a steam ejector and a gas and liquid contact chamber and said vacuum section capable of reducing pressure in said purifying section,
said process comprising the steps of:
    distilling an easily polymerizable compound in the distillation column and condensing the resulting distilled compound in the condenser in the purifying section,
    permitting an exhaust gas containing the easily polymerizable compound which is not condensed through the condenser, to flow into the gas and liquid contact chamber though said steam ejector in the vacuum section and
    supplying a liquid containing a polymerization inhibitor to the gas and liquid contact chamber, thereby inhibiting the polymerization in the vacuum section.

2. The process according to claim 1, wherein the vacuum section comprises at least one gas and liquid contact chamber, and supplying the liquid containing the polymerization inhibitor to the first gas and liquid contact chamber.

3. The process according to claim 2, wherein the vacuum section further comprises an ejector seal tank and the liquid containing the polymerization inhibitor is added to a liquid in the ejector seal tank.

4. The process according to claim 1, wherein the vacuum section comprises at least two gas and liquid contact chambers, and supplying the liquid containing the polymerization inhibitor to the first and the second gas and liquid contact chambers.

5. The process according to claim 1, wherein the gas and liquid contact chamber is a surface condenser, and further comprising wetting the inside surface of the condenser uniformly with the liquid.

6. The process according to claim 5, wherein the liquid is sprayed onto the overall inside surface of the surface condenser.

7. The process according to claim 1, wherein the gas and liquid chamber is a barometric condenser, and the liquid serves to cool the barometric condenser.

8. The process according to claim 1, wherein the easily polymerizable compound is (meth)acrylic acid and/or (meth)acrylate.

9. The process according to claim 1, wherein the polymerization inhibitor is at least one member selected from the group consisting of hydroquinone, methoquinone, manganese acetate, phenothiazine, nitrosophenol, cupferron, dibutyl dithiocarbamic acid copper salt and N-oxyl compounds.

* * * * *